US009464308B2

(12) United States Patent
Laayoun et al.

(10) Patent No.: US 9,464,308 B2
(45) Date of Patent: Oct. 11, 2016

(54) METHOD FOR TRANSCRIPTIONAL AMPLIFICATION OF NUCLEIC ACIDS COMBINING STEPS OF DIFFERENT TEMPERATURES

(71) Applicant: BIOMERIEUX, Marcy l'Etoile (FR)

(72) Inventors: Ali Laayoun, La Frette (FR); Alain Laurent, Grenoble (FR); Laurent Mesta, Genas (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 14/363,214

(22) PCT Filed: Dec. 14, 2012

(86) PCT No.: PCT/FR2012/052934
§ 371 (c)(1),
(2) Date: Jun. 5, 2014

(87) PCT Pub. No.: WO2013/088085
PCT Pub. Date: Jun. 20, 2013

(65) Prior Publication Data
US 2014/0356870 A1 Dec. 4, 2014

(30) Foreign Application Priority Data

Dec. 16, 2011 (FR) ...................................... 11 61758

(51) Int. Cl.
*C12Q 1/68* (2006.01)
*C12P 19/34* (2006.01)
(52) U.S. Cl.
CPC ............. *C12P 19/34* (2013.01); *C12Q 1/6813* (2013.01); *C12Q 1/6865* (2013.01)
(58) Field of Classification Search
CPC ............. C12Q 1/6865; C12Q 1/6813; C12Q 2521/107; C12Q 2521/119; C12Q 2521/327; C12Q 2527/101; C12Q 2527/125; C12P 19/34
See application file for complete search history.

(56) References Cited

U.S. PATENT DOCUMENTS

2002/0132242 A1  9/2002  Gerdes et al.

FOREIGN PATENT DOCUMENTS

| EP | 0 397 269 B1 | 11/1990 |
| EP | 0 821 059 A2 | 1/1998 |
| WO | WO 00/36112 A1 | 6/2000 |
| WO | WO 02/070735 A2 | 9/2002 |

OTHER PUBLICATIONS

Fahy et al., "Self-sustained sequence replication (3SR): an isothermal transcription-based amplification system alternative to PCR," Genome Research, 1991, vol. 1, pp. 25-33.*

Lee et al., "The Stabilization of Proteins by Sucrose", *The Journal of Biological Chemistry*, Jul. 25, 1981,vol. 256, No. 14, pp. 7193-7201.
Bernier et al., "Stabilization of B-glucosidase by Polyhydric Alcohols", *Journal of Biotechnology*, 1988, vol. 7, pp. 293-298.
Carninci et al., "Thermostabilization and Thermoactivation of Thermolabile Enzymes by Trehalose and its Application for the Synthesis of Full Length cDNA", *Proceedings of the National Academy of Sciences*, Jan. 1, 1998, vol. 95, pp. 520-524.
Spiess et al., "Trehalose is a Potent PCR Enhancer: Lowering of DNA Melting Temperature and Thermal Stabilization of Taq Polymerase by the Disaccharide Trehalose", *Clinical Chemistry*, 2004, vol. 50, No. 7, pp. 1256-1259.
Nakahara et al., "Inosine 5'-triphosphate Can Dramatically Increase the Yield of NASBA Products Targeting GC-rich and Intramolecular Base-Paired Viroid RNA", *Nucleic Acids Research*, 1998, vol. 26, No. 7, pp. 1854-1855.
Gill et al., "Nucleic Acid Isothermal Amplification Technologies-A Review", *Nucleosides, Nucleotides, and Nucleic Acids*, 2008 vol. 27, pp. 224-243.
Spiess et al., "A Highly Efficient Method for Long-Chain cDNA Synthesis Using Trehalose and Betaine", *Analytical Biochemistry*, Feb. 15, 2002, vol. 301, No. 2, pp. 168-174.
Weigl et al., "Non-instrumented Nucleic Acid Amplification Assay", *Proceedings of SPIE*, Jan. 1, 2008, vol. 6886, pp. 688604-1-688604-12.
Ge et al., "Detection of Novel Swine Origin Influenza a Virus (H1N1) by Real-Time Nucleic Acid Sequence-Based Amplification", *Journal of Virological Methods*, Feb. 1, 2010, vol. 163, No. 2, pp. 495-497.
Mizuno et al., "Increased Specificity of Reverse Transcription Priming by Trehalose and Oligo-Blockers Allows High-Efficiency Window Separation of mRNA Display", *Nucleic Acids Research*, Jan. 1, 1999, vol. 27, No. 5, pp. 1345-1349.
Langabeer et al., "Transcription-Mediated Amplification and Hybridisation Protection Assay to Determine BCR-ABL Transcript Levels in Patients with Chronic Myeloid Leukaemia", *Leukemia*, Jan. 1, 2002, pp. 393-399.
Leone et al., "Molecular Beacon Probes Combined with Amplification by NASBA Enable Homogeneous, Real-Time Detection of RNA", *Nucleic Acids Research*, 1998, vol. 26, No. 9, pp. 2150-2155.
May 2, 2013 International Search Report issued in PCT/FR2012/052934.
May 2, 2013 Written Opinion issued in PCT/FR2012/052934.

* cited by examiner

*Primary Examiner* — Young J Kim
(74) *Attorney, Agent, or Firm* — Oliff PLC

(57) ABSTRACT

A method of transcriptional amplification includes: (a) obtaining a mixture by combining (i) a biological sample comprising nucleic acids, (ii) amplification primers, (iii) amplification reagents including enzymes required for amplification, and (iv) at least one polyol capable of stabilizing the enzymes required for amplification; (b) denaturing the nucleic acids by heating the mixture at a temperature above 41° C.; and (c) transcriptionally amplifying at least one target nucleic acid at a temperature above 41° C. when present in the mixture.

14 Claims, 6 Drawing Sheets

Figure 1A:
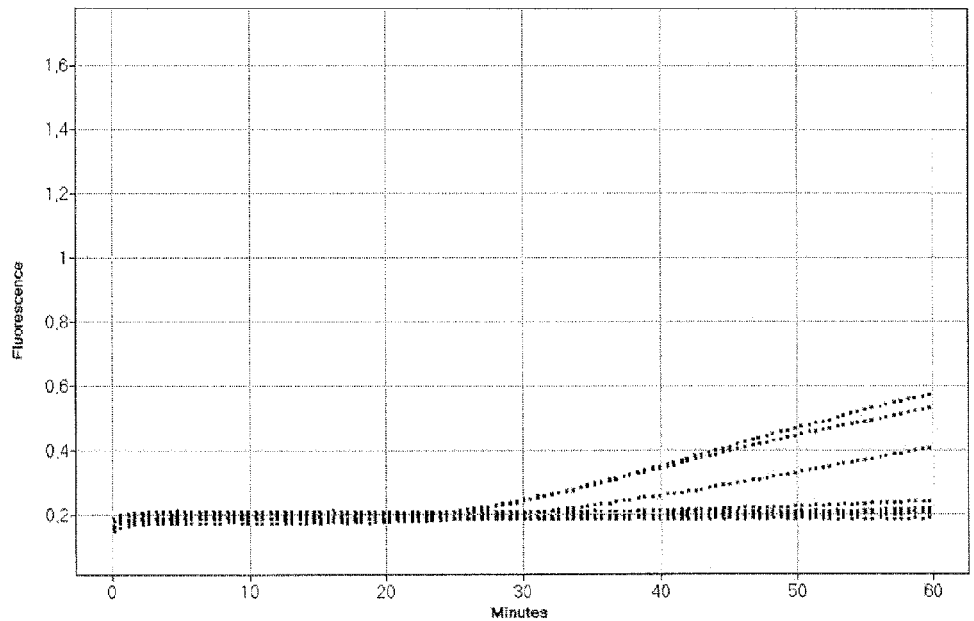
Figure 1B:
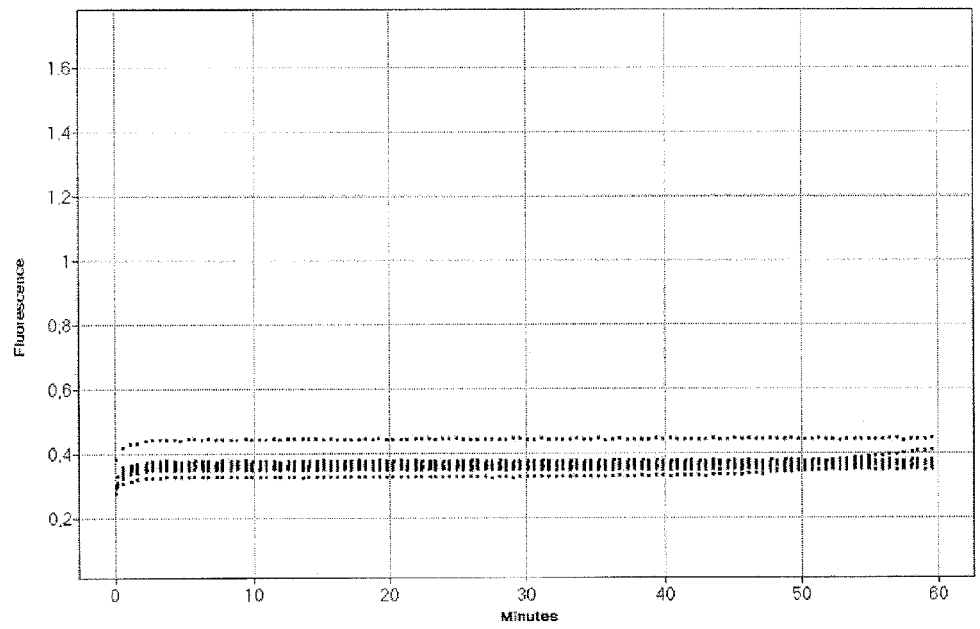
Figure 1C:
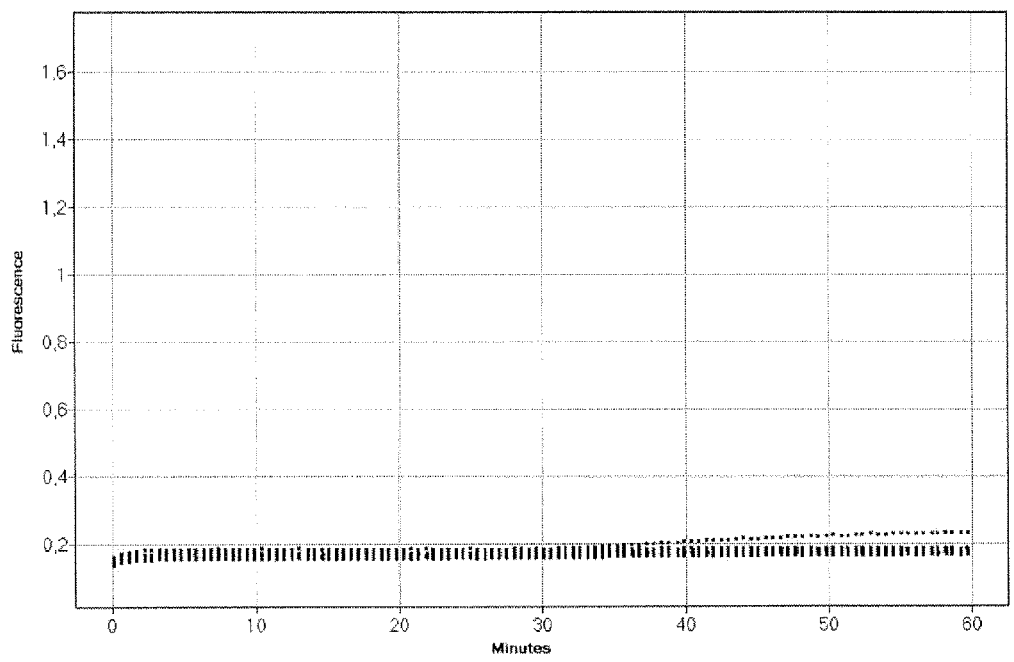
Figure 1D:
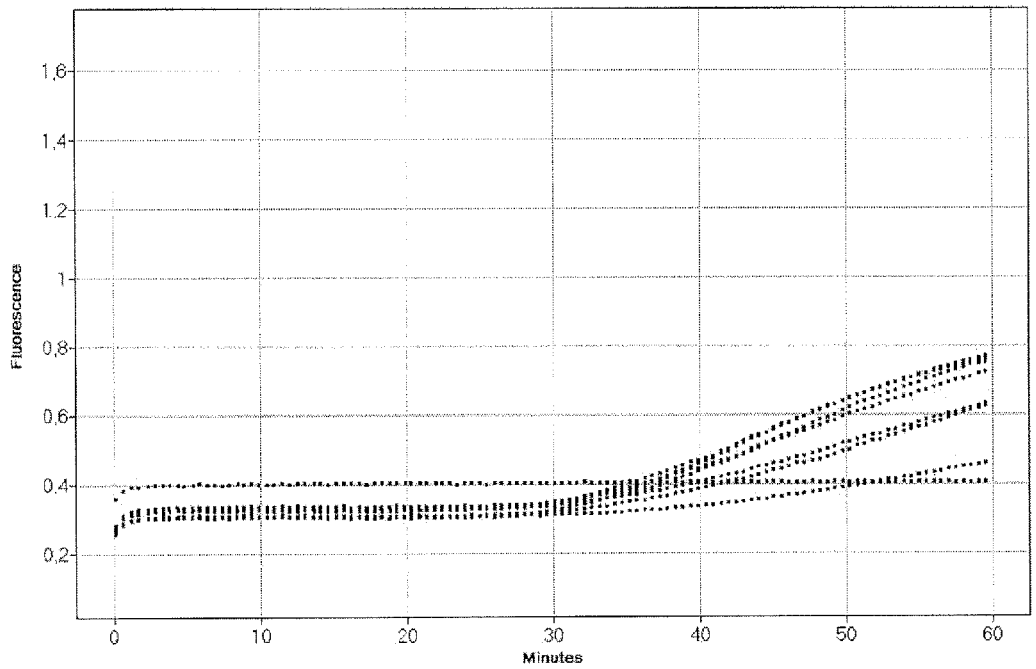
Figure 1E:
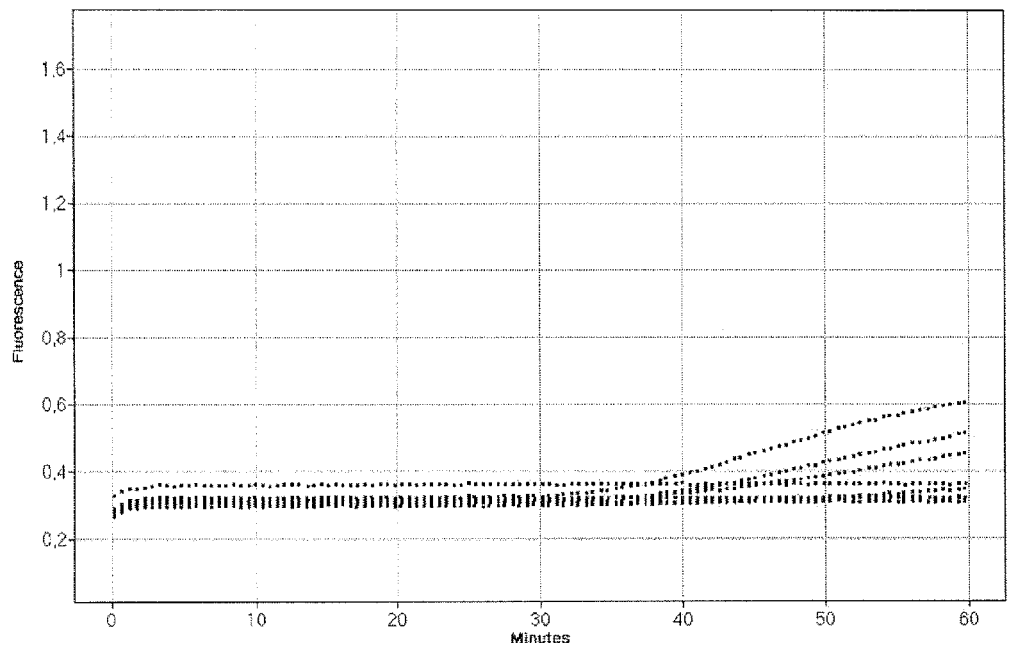
Figure 1F:
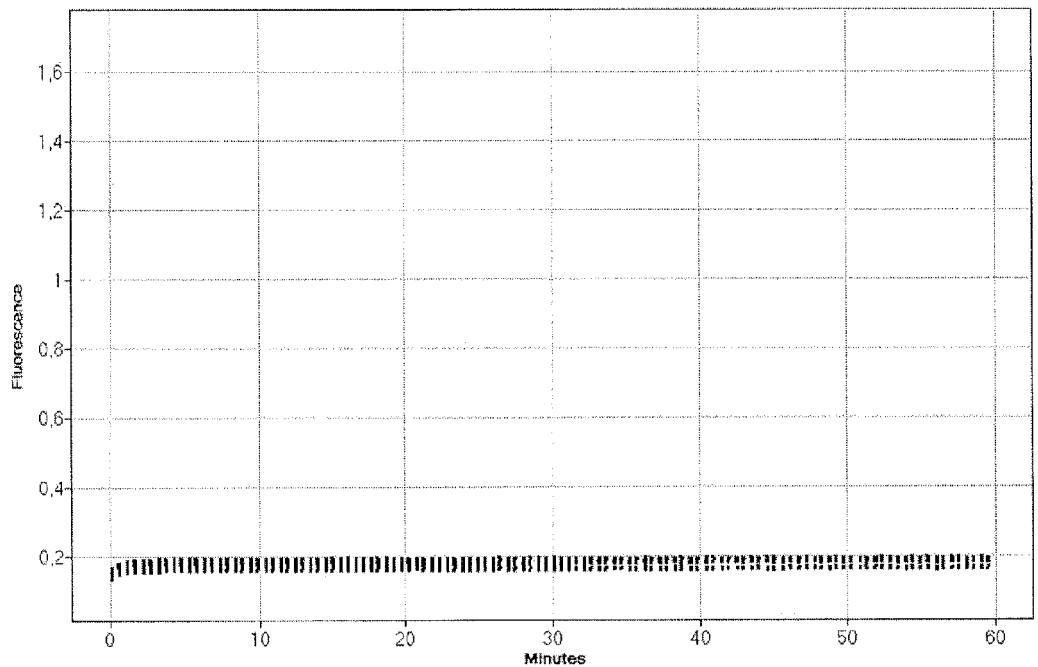

METHOD FOR TRANSCRIPTIONAL AMPLIFICATION OF NUCLEIC ACIDS COMBINING STEPS OF DIFFERENT TEMPERATURES

The present invention relates to a method in which at least one target nucleic acid, present in a biological sample, is amplified by means of a method of transcriptional amplification which makes it possible to combine steps of different temperatures, namely the denaturation and the amplification per se.

The prior art is made up of a certain number of scientific papers which address the thermostabilizing effect of polyols on enzymes; this is in particular the case for:

Lee in 1981 in J. Biol. Chemistry 256(14): 7193-7201, entitled: "The stabilization of proteins by sucrose", which describes the thermostabilizing effect of sucrose on α-chymotrypsin, chymotrypsinogen and RNAse.

Bernier in 1988 in J. Biotechnol. 7: 293-298, having the title: "Stabilization of α-glucosidase by polyhydric alcohols" demonstrating thermostabilizing effect of polyols on α-glucosidase.

Carninci in 1998 in Proc. Natl Acad. Sci. 95: 520-524, entitled: "Thermostabilization and thermoactivation of thermolabile enzymes by trehalose and its application for the synthesis of full length cDNA" which presents the thermostabilization by trehalose of reverse transcription enzymes and of restriction enzymes.

Spiess in 2004 in Clinical Chemistry 50 (7): 1256-1259, which has the title "Trehalose is a potent PCR enhancer: lowering of DNA melting temperature and thermal stabilization of tag polymerase by disaccharide trehalose", in which the thermostabilizing effect of trehalose on the Tag polymerase is demonstrated.

It is therefore clear that, for about thirty years, a large number of researchers have been interested in the thermostabilizing effect of polyols on enzymes. Moreover a patent application was filed fifteen years ago, under number EP-A-0 821 058, which provides a method for improving an enzymatic activity at high temperature. The corresponding patent claims the use of polyols for thermostabilizing a polymerase and a restriction enzyme.

Despite the interest of scientists, it appears that no-one has attempted to adapt this approach to transcriptional amplification technologies of the NASBA, TMA, etc., type which, in order to operate, make use of several different enzymatic activities. The first step consists of the denaturation of the target, a nucleic acid, generally a ribonucleic acid (RNA), at 65° C. for 2 minutes, and the second step itself consists in adding enzymes required for isothermal amplification at 41° C. These two steps make the method technically restrictive for the user by virtue of the use of two successive temperatures.

Furthermore, the use of a single temperature (41° C.) currently poses various problems such as the amplification of targets rich in guanine and cytosine which have secondary structures that are difficult to amplify. The most well-known solution for making these secondary structures easy to amplify using transcriptional amplification techniques is the use of a fifth nucleotide in the amplification mixture, which is riboinosine triphosphate (K Nakahara et al. Nucleic Acids Res. 1998 Apr. 1; 26(7): 1854-1856).

Deoxyribonucleic acid (DNA) targets can be easily used with the NASBA technology. To do this, all that is needed is, for example, to apply beforehand to the treated sample a method according to EP-B-0 397 269 or according to patent application WO-A-02/070735, in order to enable the amplification of the DNA targets.

Although those skilled in the art have used this type of transcription of DNA targets with two steps of different temperatures for decades, they have not yet thought to try to improve the thermostability of the enzymes used in order to reduce the restrictions of this type of transcriptional amplification method.

The present invention therefore describes a simplification of the transcriptional amplification method which is then carried out in a single step by virtue of the simultaneous addition of the target nucleic acid and of the amplification reagents, such as buffers, enzymes or nucleotides, in the presence of thermostabilizing chemical additives, which enable the use of a higher amplification temperature with an alignment with the temperature of the step of denaturation of said targets. This is an effect which is particularly unexpected and therefore surprising.

The novelty lies in the simultaneous thermostabilization of all the enzymatic activities, in particular of the three enzymatic activities present in the NASBA amplification method, through the use of chemical additives such as polyols making it possible to preserve the activities of T7 RNA polymerase, RNAse H and AMV-RT at temperatures higher than 41° C., and thus making it possible to combine the experimental steps of denaturation and amplification.

The present invention provides a transcriptional amplification method in which:

a) at least one target nucleic acid, present in a biological sample, is placed in the presence:
  of amplification primers,
  of all the reagents required for carrying out the amplification, including the enzymes participating in the amplification, and
  of at least one polyol which makes it possible to stabilize the enzymes required for carrying out the amplification,
b) the mixture is heated at a temperature above 41° C.,
c) a transcriptional amplification of the target nucleic acid is carried out at a temperature above 41° C.

According to one embodiment of the amplification method, the temperature at which the amplification is carried out is between 41 and 49° C.

According to another embodiment of the amplification method, the temperature at which the amplification is carried out is above or equal to 46° C.

Whatever the embodiment of the amplification method, the enzymatic activities provided by the enzymes are:
  the RNA polymerase activity (T7, SP6, etc.),
  the reverse transcriptase activity (AMV-RT, MMLV-RT, etc.), and
  the RNAse H activity.

The RNAse H activity can be given by an independent enzyme ("individual" activity) or by an enzyme having another enzymatic activity ("combined" activity). This other activity combined with RNAse H may be given by a reverse transcriptase enzyme or an RNA polymerase or a different enzyme.

The enzymatic activities make it possible to carry out isothermal amplifications, such as:
  NASBA (nucleic acid sequence-based amplification),
  TMA (transcription-mediated amplification),
  3SR (self-sustained sequence replication),
  SMART (signal-mediated amplification of RNA technology),
  MDA (multiple displacement amplification), and any other isothermal amplifications involving at least one of the three activities mentioned above and used for whole genome amplifications or for amplifications of a specific DNA or RNA sequence.

Whatever the embodiment of the amplification method, the polyol(s) consist(s) of one of the compounds or a combination of the compounds which follow:
lactose,
sorbitol,
sucrose,
mannitol, and
trehalose.

Whatever the embodiment of the amplification method, the concentration of polyol(s) is between 0.4 and 1.5 M.

The present invention also relates to a method for detecting amplicons obtained by means of the amplification method, as described above, which consists in adding, during step a), at least one type of detection probe per target nucleic acid which is sought and which may be present in the biological sample, and in carrying out the following additional step:
 d) the detection of the presence of amplicons resulting from the amplification carried out in step c) is carried out by hybridization of the probe on each amplicon in solution.

The present invention also relates to a method for pretreating the target nucleic acid(s) which is (are) sought and which may be present in the biological sample, and which must be amplified, as described above, consisting in carrying out the following additional step, before step a), in which said biological sample is subjected to a temperature below or equal to 65° C. for RNA and to a temperature below or equal to 95° C. for DNA.

The present invention also relates to a method for pretreating the target nucleic acid(s) which is (are) sought and which may be present in the biological sample, and which must be amplified, as described above, consisting in carrying out an additional step, before step a), in which said biological sample is subjected to a temperature below or equal to 49° C.

The present invention also relates to a method for the diagnosis, in vitro, of the presence of one type or of various types of target nucleic acids which are sought and which may be present in the biological sample, consisting:
 a) in carrying out a pretreatment method, as described above,
 b) in carrying out an amplification method, as described above,
 c) in carrying out a detection method, as described above.

According to one embodiment of the diagnosis method, all of the method is carried out in a single container.

According to a first embodiment variant of the above method, all of the method is carried out at a single temperature above 41° C.

According to a first embodiment variant of the above method, all of the method is carried out at a single temperature of between 46 and 49° C.

The figures appended hereto are given by way of explanatory example and have no limiting nature. They will make it possible to understand the invention more clearly.

The FIG. 1 represent the functional screening of thermostabilizing compounds during NASBA amplifications at 46° C. in the presence of 7.5 cps/reaction of HIV-1B transcript (seven replicas per screening), with in:
 FIG. 1A a lactose concentration of 0.21 M,
 FIG. 1B a maltose concentration of 0.9 M,
 FIG. 1C a raffinose concentration of 0.05 M,
 FIG. 1D a sorbitol concentration of 1.2 M,
 FIG. 1E a sucrose concentration of 0.6 M, and
 FIG. 1F a turanose concentration of 1.09 M.

Figure 2:
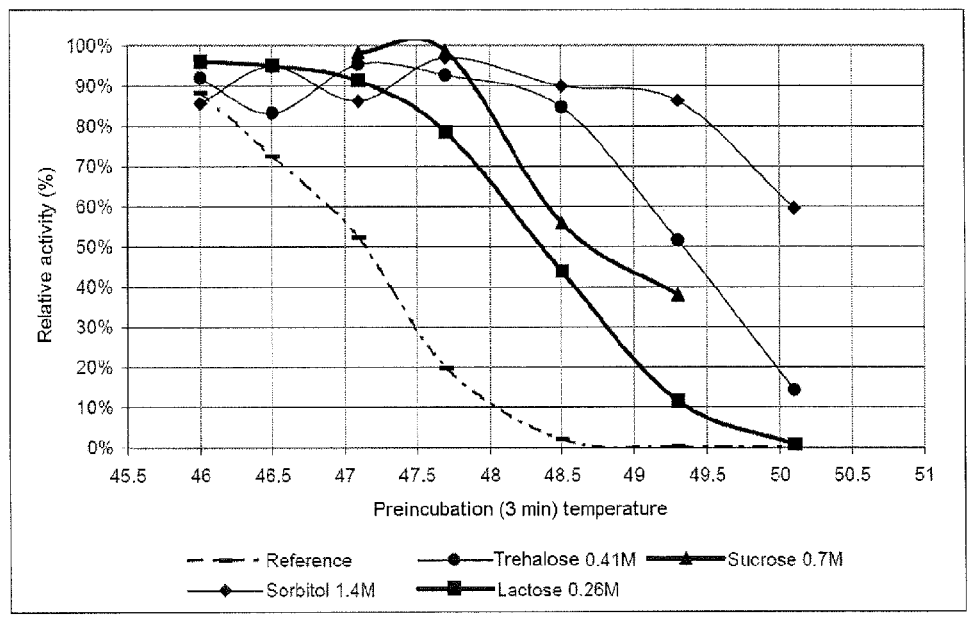

FIG. 2 describes the residual activity (%) of T7 RNA polymerase after 3 minutes of preincubation at various temperatures and in the presence of various thermostabilizing compounds.

Figure 3A:
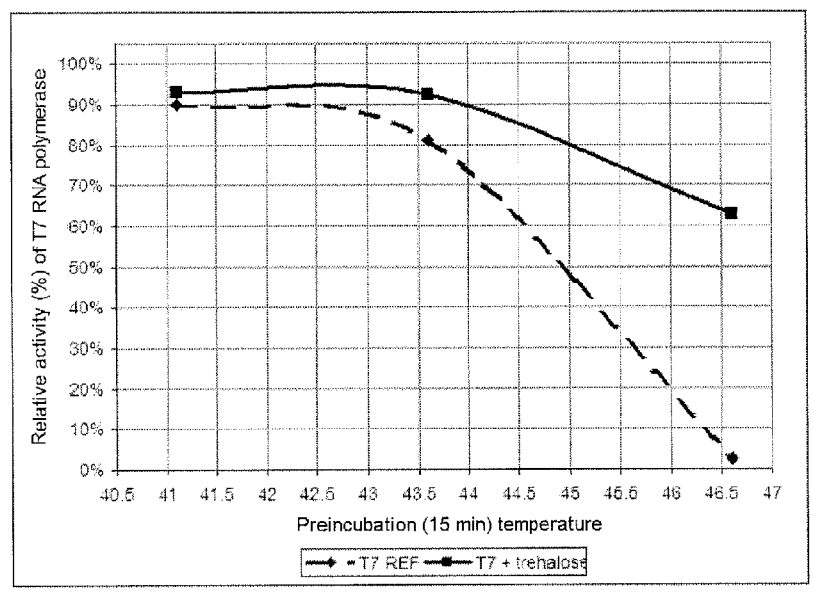

FIG. 3A describes the residual activity of T7 RNA polymerase after 15 minutes of preincubation at various temperatures, with or without 0.4 M trehalose.

Figure 3B:
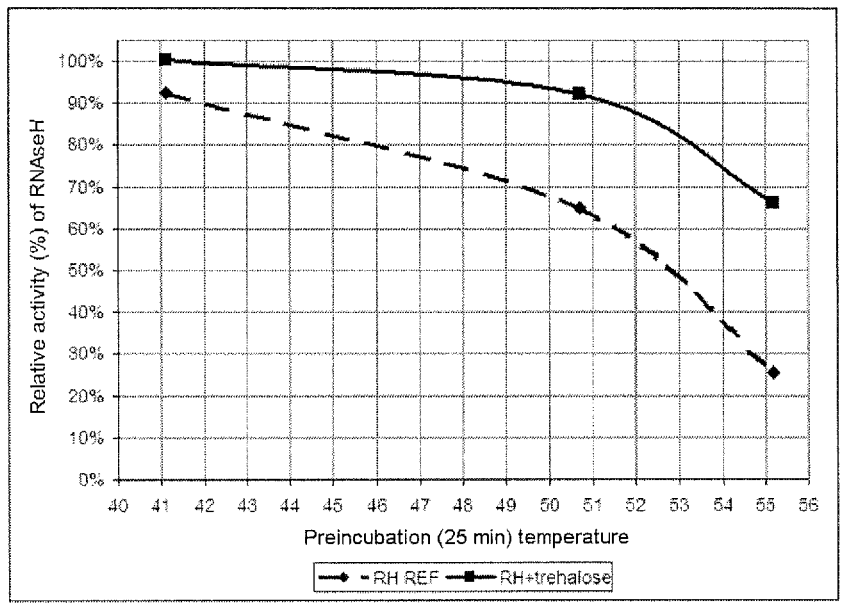

FIG. 3B describes the residual activity of RNAse H after 25 minutes of preincubation at various temperatures, with or without 0.4 M trehalose.

Figure 3C:
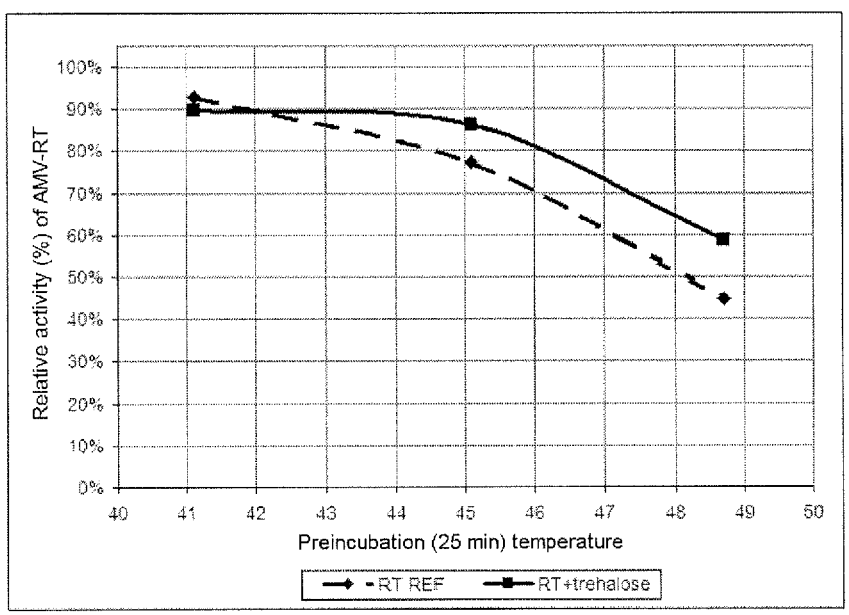

FIG. 3C describes the residual activity of AMV-RT after 25 minutes of preincubation at various temperatures, with or without 0.4 M trehalose.

Figure 4:
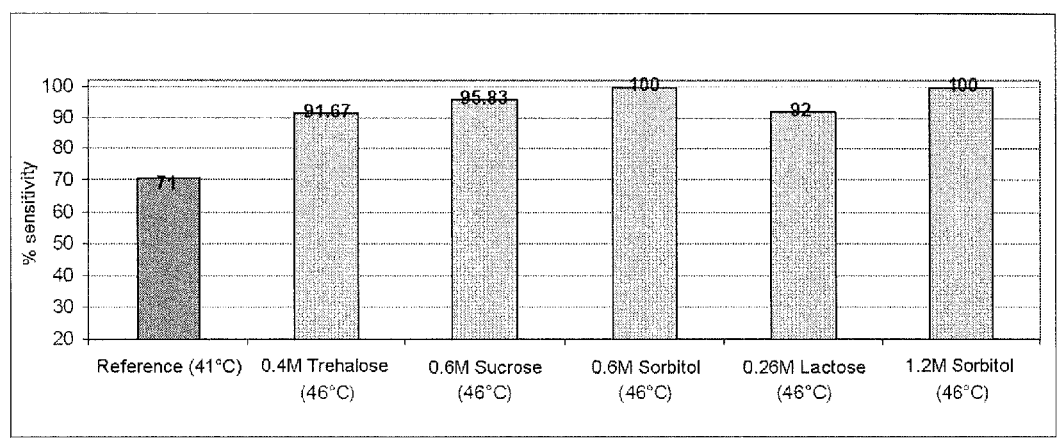

FIG. 4 gives the measurement of the sensitivity (%) obtained in the presence of various thermostabilizing compounds during an HIV-1 type B NASBA amplification at 5 cps/test and without target denaturation phase (N=24). It should be noted that, at 46° C., the reference which does not benefit from thermostabilizing additives no longer makes it possible to obtain amplification.

Although the use of sugars and more generally of polyols for thermostabilizing the enzymes is a piece of information that could be found in the literature, their use at high concentrations in a transcriptional amplification, such as NASBA, for producing an isothermal amplification at more than 41° C., in particular at more than 44° C. and preferentially at more than 46° C., with a possible preincubation up to 49° C., is a technical advance which makes it possible to technically simplify this type of amplification for the end user.

Although it operates between 41 and 45° C., it is in particular necessary to increase the NASBA amplification temperature to 46° C. in order to facilitate the denaturation of structured targets, thus making it possible to improve detection performance levels.

The examples below use the NASBA (Nucleic Acid Sequence-Based Amplification) transcriptional and isothermal amplification method. However, the approach described in this document is also applicable to other isothermal amplification methods such as TMA (Transcription-Mediated Amplification) or 3SR (Self-Sustained Sequence Replication) for example (Gill and Ghaemi, 2008, Nucleosides, Nucleotides and Nucleic Acids, 27: 224-245; Leone et al. 1998, NAR, 26-9: 2150-2155).

NASBA technology is an alternative technology to PCR which allows, unlike the latter, the genetic detection of live microorganisms (bacteria, viruses, etc.) by RNA amplification. This amplification technology requires three enzymatic activities in order to operate, including T7 RNA polymerase, RNAse H and AMV-RT. Among these three enzymatic activities, T7 RNA polymerase is the most thermosensitive enzyme.

Example 1

Selection of the Thermostabilizing Compounds Compatible with the NASBA Transcriptional and Isothermal Amplification Method A set of compounds with thermostabilizing properties or assumed to have such properties was evaluated in a NASBA HIV-1 2.0 amplification test on a Nuclisens EasyQ™ amplification platform (bioMérieux, Marcy l'Etoile, France) according to the supplier's recommendations. 5 cps to 30 cps of an HIV-1 type B transcript were used as target in each reaction in the presence or absence of the compound to be evaluated.

The obtaining of an amplification in the presence of the compound at a temperature of 46° C. makes it possible to validate the compound as compatible and thermostabilizing for the NASBA reaction.

As shown by the examples of FIGS. 1A, 1B, 1C, 1D, 1E and 1F, the presence or absence of a NASBA amplification at 46° C. makes it possible to easily select the thermostabilizing compounds, such as sucrose, sorbitol and lactose, which in most cases give an amplification having a correct signal (at least four positive signals out of seven replicas). The additives thus isolated are subsequently studied more precisely.

Example 2

Selection of the Thermostabilizing Compounds by Monitoring the Thermal Denaturation of T7 RNA Polymerase by UV Spectrophotometry It is demonstrated in this example that the T7 RNA polymerase denaturation temperature (T7 Tm) increases considerably in the presence of certain chemical additives, in comparison with that of the control without additive. T7 RNA polymerase was chosen as model enzyme since it is the most sensitive to thermal denaturation; the T7 Tm without additive is 48.5° C.

A UV spectrophotometry technique is used to measure the T7 Tm values. The change in the absorbance of the protein at $\lambda=280$ nm as a function of temperature is measured. When the enzyme is heated, the solution becomes cloudy, and aggregates form which correspond to the denatured form. The Tm corresponds to the temperature for which there is 50% of native form and 50% of denatured form (first derivative of the curve absorbance=f(temperature)).

In a polypropylene flask, 4 ml of 300 mM PBS phosphate buffer (Aldrich P-4417, St Quentin Fallavier, France) are mixed with 12µl of T7 RNA polymerase enzyme (bioMérieux, Marcy l'Etoile, France) at 17 mg/ml, i.e. a final protein concentration of 0.05 mg/ml. 500 µl of T7 RNA polymerase solution at 0.05 mg/ml and 500 µl of a concentrated solution of additives (Aldrich, St Quentin Fallavier, France) or of 300 mM PBS for the control are then placed in a quartz cuvette for UV spectrophotometry. After homogenization, the change in absorbance at $\lambda=280$ nm is measured as a function of temperature, between 30 and 65° C. at 1° C./min, in order to determine the T7 Tm as previously described (Cary UV spectrophotometer, Varian, Les Ulis, France).

Some representative results obtained according to the method previously described are reported in Table 1 below (the $\Delta$Tm values are reported as a function of the type of additive).

TABLE 1

Summarizing table of the $\Delta$Tm measurements observed as a function of the type of additive

| Additives | | $\Delta$Tm (° C.) | CV (%) | Number of experiments |
|---|---|---|---|---|
| T7 RNA polymerase at 0.05 mg/ml | PBS, 150 mM, pH 7.5 | — | 1.6 | 26 |
| T7 RNA polymerase at 0.05 mg/ml | PBS, 150 mM, pH 7.5/Sorbitol 1M | +0.9 | 1.1 | 3 |
| T7 RNA polymerase at 0.05 mg/ml | PBS, 150 mM, pH 7.5/Sucrose 1M | +5.8 | 1.0 | 3 |
| T7 RNA polymerase at 0.05 mg/ml | PBS, 150 mM, pH 7.5/Lactose (0.35M) | +5.5 | 0.2 | 3 |
| T7 RNA polymerase at 0.05 mg/ml | PBS, 150 mM, pH 7.5/Raffinose (0.085M) | +0.5 | 0.2 | 3 |
| T7 RNA polymerase at 0.05 mg/ml | PBS, 150 mM, pH 7.5/D-Turanose (0.15M) | -4.4 | 0.1 | 2 |

It is clearly observed that heating the T7 RNA polymerase enzyme in the presence of certain additives, such as sorbitol, sucrose or lactose, makes it possible to very significantly increase the denaturation temperature of the enzyme, by several degrees, thereby confirming its thermostabilization.

Example 3

Measurement of Thermostability ($T_{1/2}$) at 46° C. for T7 RNA Polymerase

In this example, the values of $T_{1/2}$ of T7 RNA polymerase are determined in the presence or absence of polyols. A description of the measurement method is given below, as are the various reagents used.

| Buffer A | Buffer B | Buffer C | Buffer D |
|---|---|---|---|
| 20 mM KH$_2$PO$_4$/K$_2$HPO$_4$, pH 7.5 100 mM NaCl 1M trehalose 1 mM EDTA 0.268% (v/v) triton X-100 0.1 mg/ml BSA 1 mM DTT | 20 mM Tris-HCl, pH 7.5 300 mM KCl 1M trehalose 7 mM EDTA 0.21% (w/v) triton X-100 0.2 mg/ml BSA 1 mM DTT 20 mM magnesium acetate | 200 mM KH$_2$PO$_4$/K$_2$HPO$_4$, pH 7.2 1M trehalose 0.21% (w/v) triton X-100 1 mM DTT | 3.2 mM Tris-HCl, pH 7.5 6.4 mM NaCl 0.13 mM DTT 1.3 mg/ml BSA 340 mM trehalose |

Solution W1:

Mix buffers B, C and D according to the following proportions with the following Nuclisens™ HIV-1 2.0 reagents (ref.: 285033, bioMérieux, Marcy l'Etoile, France) (for eight reactions):

36.08 μl buffer A
6.32 μl buffer B
25.36 μl buffer C
173.6 μl buffer D
eight "Nuclisens™ HIV-1 2.0 accusphere reagent"
960 μl of "Nuclisens™ HIV-1 2.0 diluent reagent".
Solution S (substrate mix):
Tris-HCl at 70 mM, pH 8.5
dNTP at 1.3 mM each
rATP, rCTP and rUTP at 2.6 mM each
rGTP at 2 mM
rITP at 0.6 mM
Sucrose at 60 mM
Mannitol at 40 mM
Dextran T-40 at 7 g/l
$MgCl_2$ at 16 mM
KCl at 320 mM
DTT at 20 mM
DMSO at 3.5 M
MB1 Molecular beacon (SEQ ID NO: 3) between 0.1 and 0.3μM
T7-Min oligonucleotide (SEQ ID NO: 1) between 10 nM and 20 nM
T7-plus oligonucleotide (SEQ ID NO: 2) between 10 nM and 20 nM.
Sequences used (5'-3' orientation):

```
T7-min (SEQ ID    AATTCTAATACGACTCACTATAGTATGAGGGCAG
NO: 1)            CAGACATCGAATTT T7-plus (SEQ ID   AAATTCGATGTCTGCTGCCCTCATACTATAGTGA
NO: 2)            GTCGTATTAGAATT MB1(SEQ ID        FAM-CTATCCCTTCGATGTCTGCTGCCCTCG-
NO: 3)            GGATAG-Dabcyl
```

1. The enzymes to be evaluated are diluted in such a way as to have a volumetric activity of 109 kU/ml.
2. A volume of 20 μl of the enzyme to be evaluated is diluted in 840 μl of solution W1.
3. 114 μl of the compound to be evaluated are then added to 193.5 μl of enzymatic mix described in point 2 above.
4. 12 portions of 20 μl of the mix that was produced in point 3 are prepared and are distributed into 0.2 ml tubes and incubated at the temperature of 46° C. in a thermocycler. One tube is removed from the thermocycler every 10 minutes for 110 minutes and is stored at 4° C. before measurement of the residual enzymatic activity.
5. 20 μl of solution S are added to 5 nl of this preincubated mixture in order to measure the rate of increase in fluorescence between 5 and 10 minutes, associated with the residual activity of the enzyme.
6. The residual activity of each T7 RNA polymerase is expressed as percentage of the fraction of enzyme having not been preincubated and corresponding to 100% activity according to the following calculation:
   $\rho_N$=slope obtained between 5 and 10 min for the T7 RNA polymerase not preincubated,
   $\rho_T$=slope obtained between 5 and 10 min for the T7 RNA polymerase preincubated at 46° C. in the presence or absence of polyols, and
   % relative activity=% $(\rho_T/\rho_N)$.
7. The $T_{1/2}$ value corresponds to the time required for the enzyme to then have only 50% of its initial activity.
The results of measuring $T_{1/2}$ of T7 RNA polymerase are described in Table 2:

TABLE 2

$T_{1/2}$ thermostability values for T7 RNA polymerase at 46° C.

| | Final molarity | $T_{1/2}$ 46° C. (min) |
|---|---|---|
| Reference | — | 7 |
| Trehalose | 0.40 | 63 |
| Lactose | 0.26 | 17 |
| Sucrose | 0.74 | ~125 |
| Sorbitol | 1.48 | >125 |

According to Table 2, it is noted that all the chemical compounds evaluated have a thermostabilizing effect on the T7 RNA polymerase activity operating in an environment specific to NASBA. 1.48 M sorbitol generates the greatest thermostabilizing effect, while lactose has a weak thermostabilizing power on T7 RNA polymerase, even though it is visible and significant.

Example 4

Measurement of the Maximum Preincubation Temperature for Preserving the T7 RNA Polymerase Activity In this example, the maximum temperature that the T7 RNA polymerase could withstand for a preincubation of 3 minutes in the presence of thermostabilizing compounds is determined.

This step can be likened to a target predenaturation or preincubation phase. The protocol used in this example is similar to that of example 2, with the exception of the fact that the temperatures are variable and that the preincubation time was fixed at 3 minutes.

FIG. 2 shows that 0.7 M sucrose, 0.4 M trehalose and 1.4 M sorbitol make it possible to preserve 100% of the T7 RNA polymerase activity for 3 minutes at 48° C., or even 3 minutes at 49° C. for sorbitol.

Example 5

Measurement of Thermostability at Various Temperatures for T7 RNA Polymerase, RNAse H and AMV-RT in the Presence or Absence of 0.4 M Trehalose Firstly and as shown by FIGS. 3A, 3B and 3C, this example demonstrates that T7 RNA polymerase (T7) is the most thermosensitive and that the use of additive such as trehalose makes it possible to render it more thermostable. Secondly, thermostabilizing effect of trehalose on the RNAse H (RH) and AMV-RT (RT) activities is also demonstrated.

Description of the method for measuring the T7 RNA polymerase, RNAse H and AMV-RT activities for example 5:

1. The T7 RNA polymerase, RNAse H and AMV-RT enzymes are used at volumetric activities of 109 kU/ml, 1 kU/ml and 25 kU/ml respectively.
2. The T7 RNA polymerase, RNAse H and AMV-RT enzymes are diluted in the solution W1 of example 3 according to the ratios 1/43, 2/191 and 2/27 respectively, in order to mimic the physicochemical environment of the NASBA reaction.
3. A 1.1 M trehalose solution is then added to the above mixtures so as to have a final concentration of 0.4 M.

4. Portions of 20 μl of the above solution are then distributed into 0.2 ml tubes and incubated for a predetermined time at various temperatures.
5. The residual activity of each of the T7 RNA polymerase, RNAse H or AMV-RT activities is then measured by adding 5 μl of enzymatic solution to 20 μl of solution S containing the reagents corresponding to each of the activities measured.

Solution S for Measuring the T7 RNA Polymerase Activity:
Similar to example 3.

Solution S for Measuring the RNAse H Activity:
dNTP at 1.3 mM each,
rATP, rCTP, rUTP at 2.6 mM each,
rGTP at 2 mM,
rITP at 0.25 mM,
Sucrose at 60 mM,
Mannitol at 40 mM,
Dextran T-40 at 7 g/l,
MgCl$_2$ at 16 mM,
KCl at 400 mM,
DTT at 25 mM,
Tris-HCl at 80 mM, pH 8.5,
DMSO at 4.4 M, and
RNAse H probe between 0.2 and 2 μM: 5' FAM-AUAA-TAMRA 3'.

Solution S for measuring the DNA-dependent AMV-RT activity:
dNTP at 0.3 mM each,
rATP, rCTP, rUTP at 0.6 mM each,
rGTP at 0.5 mM,
rITP at 0.25 mM,
Sucrose at 15 mM,
Mannitol at 10 mM,
Dextran T-40 at 1.7 g/l,
MgCl$_2$ at 4 mM,
KCl at 800 mM,
DTT at 50 mM,
Tris-HCl at 165 mM, pH 8.5,
DMSO at 8.8 M,
MB2 molecular beacon between 0.2 and 2 μM, and having SEQ ID NO: 4:

5' ROX-GATGCGGAGCGCAGTAGACATGCATCCGAACAT
CACAGCAGACACAGCCTGGTTTT-DABCYL 3',
and

PRT oligonucleotide between 1 and 5 μM and having SEQ NO: 5:

5'-AAAACCAGGCTGTGTCTG-3'.

6. The residual activity of each mutant is expressed as percentage of the fraction of enzyme having not been preincubated and corresponding to 100% activity according to the following calculation:
$\rho_N$=slope obtained between 5 and 10 min for the enzyme not preincubated,
$\rho_T$=slope obtained between 5 and 10 min for the enzyme preincubated at various temperatures, with or without the presence of the polyol to be studied, and
percentage relative activity=% ($\rho_T/\rho_N$).

Example 6

Study of the Sensitivity of the Detection by NASBA Transcriptional Amplification Method at 46° C. And in the Presence of Thermostabilizing Compounds In this example, it is demonstrated that it is possible to carry out a NASBA amplification at 46° C. in the presence of thermostabilizing compounds and without a phase of denaturation of the HIV-1B transcripts used as targets at the concentration of 5 cps/reaction, which is the NASBA detection limit. The objective of this is to simplify the method by virtue of the simultaneous addition of the targets to the enzyme and amplification reagent mixes.

A Nuclisens™ HIV-1 2.0 amplification kit (ref.: 285033, bioMérieux, Marcy l'Etoile, France) was used to carry out the amplification experiments in the presence of trehalose, sucrose or sorbitol at the detection limit with an HIV-1 type B transcript at 5 cps/test. Each amplification is replicated 24 times in order to estimate the sensitivity of the test in the presence of thermostabilizing compounds at 46° C.

The sensitivity is expressed as percentage of positive signals determined by the EasyQ™ analysis system, relative to the total number of replicates.

FIG. 4 demonstrates the advantage of using reaction temperatures higher than 41° C. in the presence of certain polyols by virtue of the gains in sensitivity obtained, in particular with sorbitol which makes it possible to detect 100% of the HIV1-B transcripts.

The invention claimed is:

1. A method of transcriptional amplification, comprising:
   a) obtaining a mixture by combining (i) a biological sample comprising nucleic acids, (ii) amplification primers, (iii) amplification reagents including enzymes required for amplification, and (iv) at least one polyol capable of stabilizing the enzymes required for amplification;
   b) denaturing the nucleic acids by heating the mixture at a temperature of 46° C. or more; and
   c) transcriptionally amplifying at least one target nucleic acid at a temperature of 46° C. or more when present in the mixture;
   wherein the at least one polyol is selected from the group consisting of lactose, sorbitol, sucrose, trehalose, and mannitol.

2. The method according to claim 1, wherein the temperature at which the denaturation and the amplification are carried out is in a range of 46° C. to 49° C.

3. The method according to claim 1, wherein the enzymes provide RNA polymerase activity, reverse transcriptase activity, and RNAse H activity.

4. The method according to claim 1, wherein the concentration of the at least one polyol is in a range of from 0.4 to 1.5 M.

5. A method for detecting amplicons, comprising:
   carrying out the method according to claim 1 to obtain amplicons when the at least one target nucleic acid is present in the mixture such that, during step a), at least one type of detection probe per target nucleic acid sought is included in the mixture; and
   d) detecting hybridization between the at least one type of detection probe and the amplicons.

6. An in vitro diagnostic method of detecting at least one target nucleic acid when present in the biological sample, comprising:

a) pretreating the biological sample; and
   b) carrying out the method according to claim 5.

7. The method according to claim 6, wherein the entire method is carried out in a single container.

8. The method according to claim 6, wherein the entire method is carried out at a single temperature of between 46 and 49° C.

9. The method according to claim 7, wherein the entire method is carried out at a single temperature of between 46 and 49° C.

10. The method according to claim 1, further comprising pretreating the nucleic acids of the biological sample, before step a), by subjecting the biological sample to a temperature below or equal to 65° C. for RNA or to a temperature below or equal to 95° C. for DNA.

11. The method according to claim 1, further comprising pretreating the nucleic acids of the biological sample, before step a), by subjecting the biological sample to a temperature below or equal to 49° C.

12. A method of transcriptional amplification, comprising:
   a) obtaining a mixture by combining (i) a biological sample comprising nucleic acids, (ii) amplification primers, (iii) amplification reagents including enzymes required for amplification, and (iv) at least one polyol capable of stabilizing the enzymes required for amplification;
   b) denaturing the nucleic acids by heating the mixture at a temperature above 41° C.; and
   c) transcriptionally amplifying at least one target nucleic acid at a temperature above 41° C. when present in the mixture;
   wherein:
   the entire method including the denaturation and the transcriptional amplification is carried out at a single temperature above 41° C.; and the at least one polyol is selected from the group consisting of lactose, sorbitol, sucrose, trehalose, and mannitol.

13. The method according to claim 12, wherein the entire method is carried out at a single temperature above 44° C.

14. The method according to claim 12, wherein the temperature at which the entire method is carried out is above 41 and less than 49° C.

* * * * *

SEQUENCE LISTING

<160> NUMBER OF SEQ ID NOS: 5

<210> SEQ ID NO 1
<211> LENGTH: 48
<212> TYPE: DNA
<213> ORGANISM: Human immunodeficiency virus

<400> SEQUENCE: 1
aattctaata cgactcacta tgtatgagg gcagcagaca tcgaattt           48

<210> SEQ ID NO 2
<211> LENGTH: 48
<212> TYPE: DNA
<213> ORGANISM: Human immunodeficiency virus

```
<400> SEQUENCE: 2
aaattcgatg tctgctgccc tcatactata gtgagtcgta ttagaatt          48

<210> SEQ ID NO 3
<211> LENGTH: 33
<212> TYPE: DNA
<213> ORGANISM: Human immunodeficiency virus

<400> SEQUENCE: 3
ctatcccttc gatgtctgct gccctcggga tag                          33

<210> SEQ ID NO 4
<211> LENGTH: 56
<212> TYPE: DNA
<213> ORGANISM: Human immunodeficiency virus

<400> SEQUENCE: 4
gatgcggagc gcagtagaca tgcatccgaa catcacagca gacacagcct ggtttt  56

<210> SEQ ID NO 5
<211> LENGTH: 18
<212> TYPE: DNA
<213> ORGANISM: Human immunodeficiency virus

<400> SEQUENCE: 5
aaaaccaggc tgtgtctg                                           18
```